United States Patent [19]

Buford, III et al.

[11] Patent Number: 5,067,956
[45] Date of Patent: Nov. 26, 1991

[54] APPARATUS FOR FASTENING A MEDICAL IMPLANT

[75] Inventors: Thomas B. Buford, III; Robert Brosnahan, both of Germantown; Scott Robinett; James Clark, both of Memphis, all of Tenn.

[73] Assignee: Smith & Nephew Richards Inc., Memphis, Tenn.

[21] Appl. No.: 513,640

[22] Filed: Apr. 24, 1990

[51] Int. Cl.$^5$ .............................................. A61B 17/58
[52] U.S. Cl. .......................................... 606/73; 606/60
[58] Field of Search ...................... 606/69, 72, 73, 60; 623/16, 18–23

[56] References Cited

U.S. PATENT DOCUMENTS

| | | | |
|---|---|---|---|
| 3,896,504 | 7/1975 | Fischer | 606/73 X |
| 4,648,388 | 3/1987 | Steffee | 606/73 X |
| 4,838,391 | 6/1989 | Branemark et al. | 623/20 |
| 4,870,957 | 10/1989 | Goble et al. | 606/73 |

FOREIGN PATENT DOCUMENTS

| | | | |
|---|---|---|---|
| 2233973 | 1/1975 | France | 606/69 |
| 2254298 | 7/1975 | France | 606/73 |
| 669898 | 4/1989 | Switzerland | 606/73 |
| 584855 | 12/1977 | U.S.S.R. | 606/73 |

Primary Examiner—Robert A. Hafer
Assistant Examiner—Kevin G. Rooney
Attorney, Agent, or Firm—Kirkpatrick & Lockhart

[57] ABSTRACT

A fixation device for fastening a medical implant to a patient'3 s bone is provided which includes a fastener with a head member and a shank and a fixation member. The shank has threads along its whole length, and has an outside diameter greater than the width of the head member. The fixation member includes a bore for receiving the fastener. The bore has a diameter intermediate the width of the head member and the outside diameter of the threads of the shank. The head member of the fastener can thus be inserted into the bore such that the uppermost thread abuts against the underside of the fixation member to prevent the fastener from backing out.

9 Claims, 3 Drawing Sheets

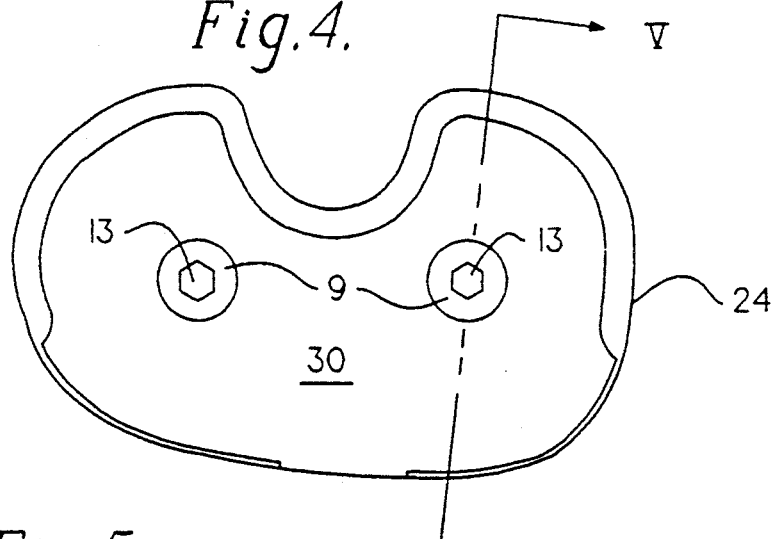
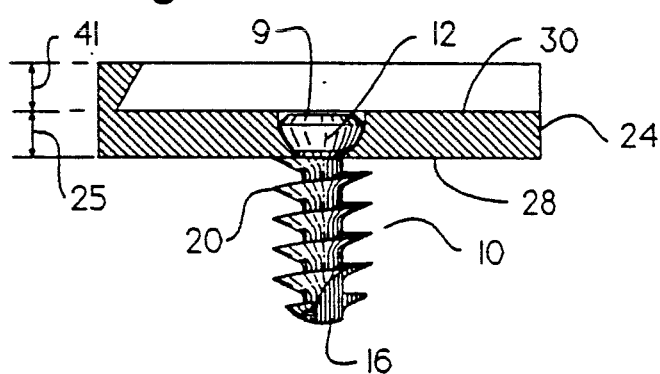
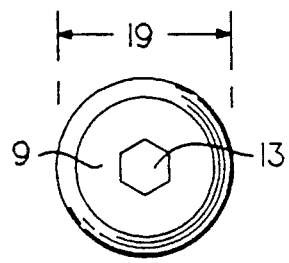
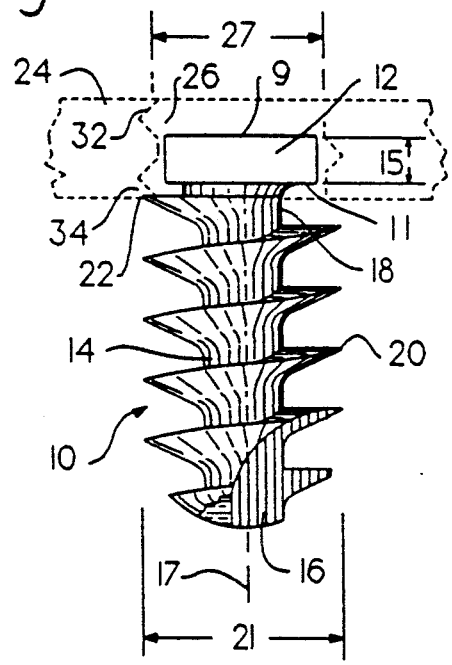
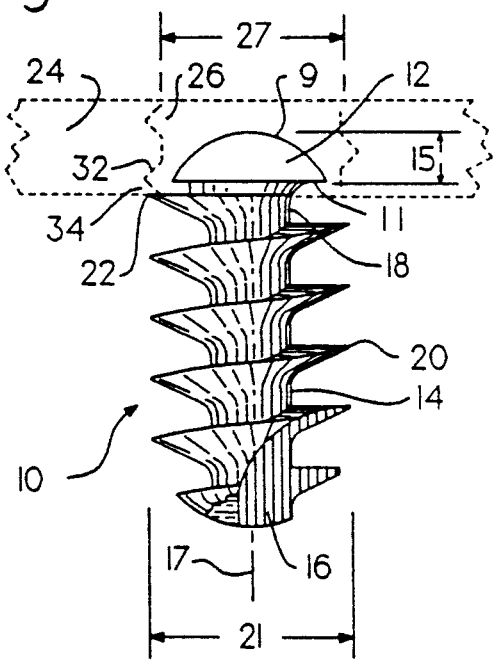

APPARATUS FOR FASTENING A MEDICAL IMPLANT

BACKGROUND OF THE INVENTION

1. Field of the Invention

The present invention is directed to an apparatus for fastening a medical implant to a patients's bone. Specifically, a fastener is provided which can be inserted into the bone and will not back out.

2. Description of the Prior Art

It is well known to replace various parts of the human body with prosthetic implants. In one application, a prosthetic knee is used to replace a patient's damaged natural knee. In another application, a prosthetic hip is used to replace a patients's damaged hip. Both of these applications require that the implant be attached to the patient's existing bone. Normally, the implants are attached to the patient's bone by the use of fasteners through a bore in a fixation member. In some applications a polymeric articular insert is placed over the fastener and fixation member. Due to forces of varied and often great magnitude on the patient's implant, the fasteners of the prior art often back out through the bore in the fixation member and impinge into the underside of an articular insert which may cover the fixation member. This can lead to increased wear and failure of the implant caused by the head of the fastener impinging into the articular insert.

One attempted solution to the problem is to sink the head of the fastener deeper into the fixation member. This simply requires the head to move farther before it impinges into the articular insert.

The need exists for a fastener which will not back out of the fixation member and cause failure of the implant.

SUMMARY OF THE PRESENT INVENTION

The present invention is directed to a fastener that will not back out of a fixation member regardless of the amount of movement of the implant or force to which it is subjected. The present invention includes a fastener of unitary construction having a head member and a shank. The shank has threads along its length. The outside diameter of the threads of the shank is greater than the width of the head member. The fastener is threaded into a bore in the fixation member and into the bone. The bore is threaded and has a diameter intermediate the width of the head member and the outside diameter of the threads of the shank. The head member of the fastener is configured to fit inside the bore in the fixation member. The uppermost thread, which is adjacent to the head member, is separated by a small gap from the underside of the fixation member. Therefore, the fastener cannot back out of the bone because its movement is restricted to only the distance between the uppermost thread and underside of the fixation member. When a compressive force is applied to the fixation member, and when the fixation member moves relative to the fastener, the uppermost thread will contact the underside of the fixation member. The fastener is thus prevented from moving any further. No amount of force less than an amount sufficient to break the fastener will cause the fastener to back out of the fixation member.

BRIEF DESCRIPTION OF THE DRAWINGS

In order that the present invention may be easily understood and readily practiced, a preferred embodiment will now be described, by way of example only, in conjunction with the following figures wherein:

FIG. 4 is a top plan view of a preferred embodiment of the fixation member and fastener of the present invention;

FIG. 5 is a sectional view of the fixation device of FIG. 4 taken along the line V—V;

FIG. 7 is a top view of the fastener of FIG. 6; and

FIGS. 8-10 are various embodiments of the head member of the fastener of FIG. 6.

DETAILED DESCRIPTION OF THE PREFERRED EMBODIMENTS

Figure 6:
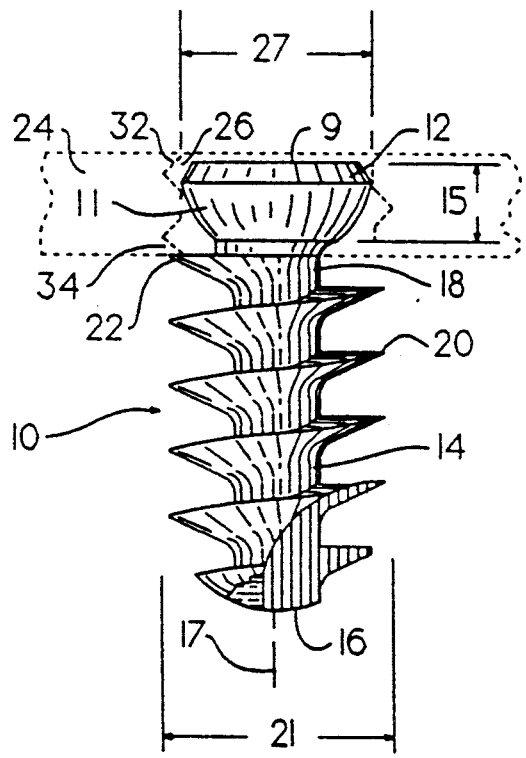
FIG. 6 is a view of the preferred embodiment of the fastener of the present invention.
Figure 8:
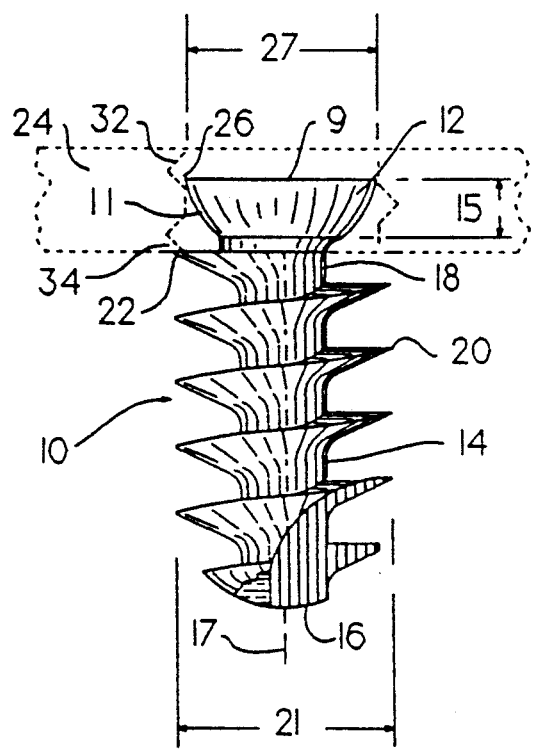

The apparatus of the present invention is comprised of a fastener 10 to be used in conjunction with a fixation member 24 and an articular insert 40. The fastener 10 as best seen in FIG. 6 is of unitary construction and has a shank 14 and a head member 12 with an underside 11 and an upperside 9. The head member 12 is shown with a hex socket 13 for receiving a tool so that it may be inserted into the fixation member 24 and bone. It will be understood that the head member 12 can include any of the conventional means for insertion of a tool to aid in inserting the fastener 10 into the fixation member 24 and bone, such as a slot or philips slot. The head member can have various shapes as seen in FIGS. 6 through 10. In FIG. 6, the underside 11 of the head member 12 is spherical with an upperside 9 which is flat but chamfered on the edge. In FIG. 8, the underside 11 of the head member 12 is spherical with the upperside 9 flat and perpendicular to the longitudinal axis of symmetry 17 of the shank 14. In FIG. 9, both the upperside 9 and the underside 11 of the head member 12 are flat and perpendicular to the longitudinal axis of symmetry 17. Finally, in FIG. 10, the upperside 9 is spherical and the underside 11 is flat. The head member 12 has a width 19 which is measured at its greatest value perpendicular to the longitudinal axis 17. The height 15 of the head member 12 is equal to the distance along the axis 17 from the underside 11 to the upperside 9.

The shank 14 is cylindrical and has an upper end 18 and a lower end 16. The upper end 18 is adjacent to the head member 12. The shank 14 has threads 20 along its entire length.

The fixation member 24 shown in FIG. 4 has a threaded bore 26. For illustration purposes, the fixation member is shown as a base plate for use in a prosthetic knee. However, it will be understood by one skilled in the art that the fixation member 24 could be used in any application which requires attaching an object to a bone. Such applications include prosthetic shoulders, elbows, hips, as well as bone plates which attach to long bones in the body. The fixation member 24 has an underside 28 which contacts the patient's bone, and an upperside 30 constructed to receive articular insert 40 as discussed hereinafter. The fixation member 24 can be of any thickness 25 less than the height 15 of the head member 12. The diameter 27 of the bore 26 is intermediate the width 19 of the head member 12 and the outside diameter 21 of the shank 14 so that the head member 12 may fit inside the bore 26. The threads in the bore 26 correspond to the threads 20 of the shank 14. The fastener 10 can thus be threaded into the bore 26 so that the head member 12 enters the bore 26 as seen in FIG. 5. The fastener 10 is securely fastened into the bone. The spiral recess 32 defining the internal threads of bore 26 terminate immediately above the underside 28 of fixation member 24 such that a lip 34 is formed where the recess 32 meets underside 30. The uppermost thread 22 of shank 14 is separated from the underside 30 by a small gap and will abut against the underside 30 if the fastener 10 begins to back out lip 34 and is thereby prevented from backing out of fixation member 24.

Figure 1:
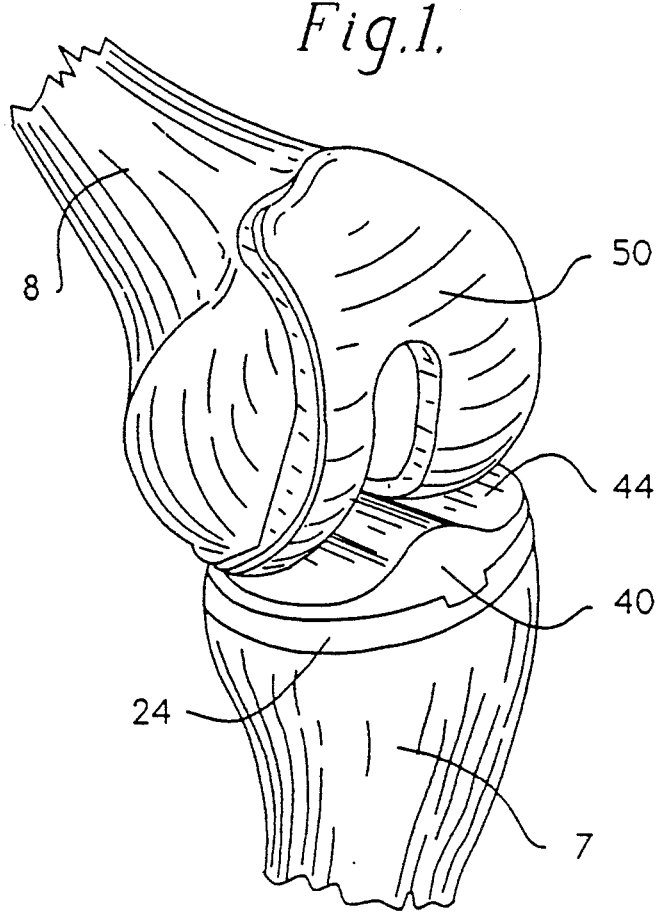
FIG. 1 is a perspective view of a prosthetic knee.
Figure 2:
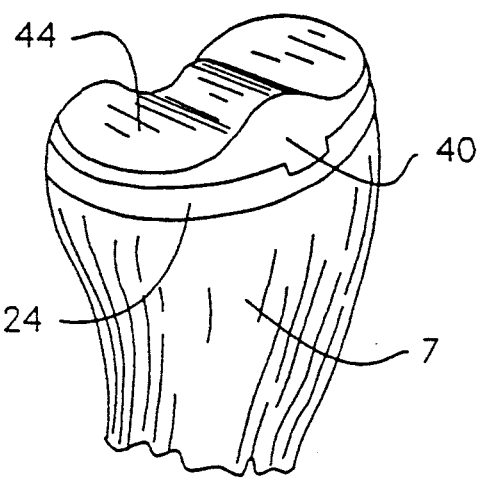
FIG. 2 is a perspective view of a fixation member and an articular insert attached to a human tibia.
Figure 3:
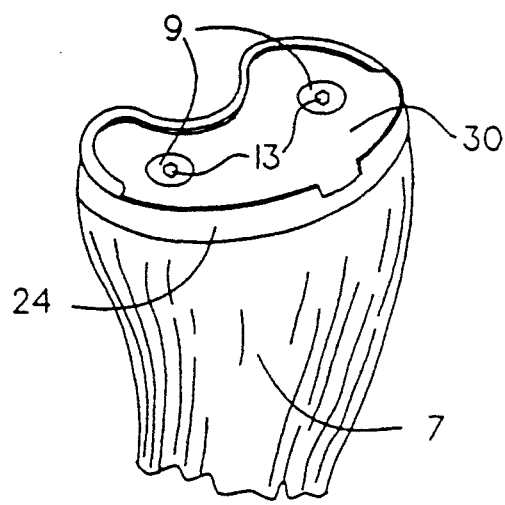
FIG. 3 is a perspective view of a fixation member attached to a human tibia.
Figure 11:
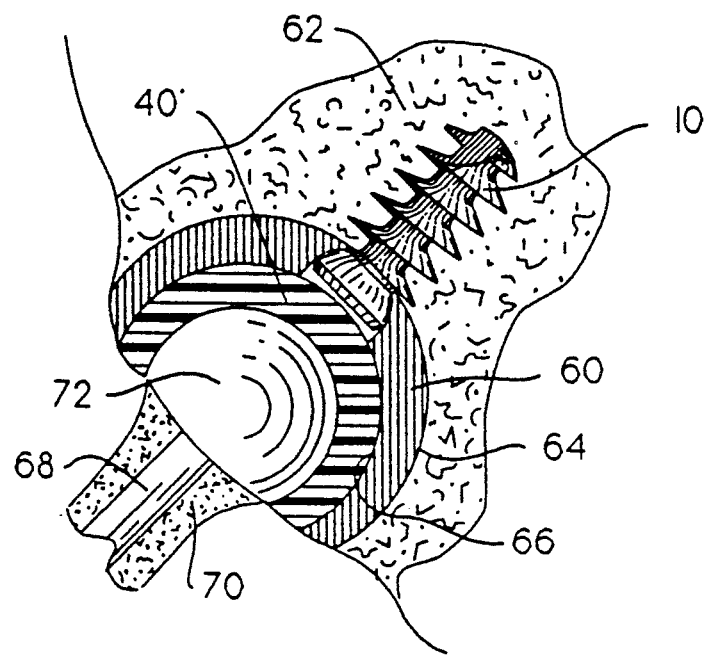
FIG. 11 is a cut away view of a prosthetic hip.

Covering the fixation member 24 is a articular insert 40 as seen in FIG. 2. The articular insert 40 has an inside surface 42 and a bearing surface 44. The thickness 41 of the articular insert 40 varies with the application and the anatomy of the patient. The inside surface 42 of the articular insert 40 contacts the outside surface 30 of the fixation member 24. Depending on the type of prosthetic implant involved, the bearing surface 44 may be subject to extreme compressive force tending to depress the fixation member 24 into the bone. For example, when used in a prosthetic knee, as seen in FIG. 1, a femoral component 50 articulates on the bearing surface 44. The femoral component 50 attaches to the femur 8 in a patient and the fixation member 24 attaches to the tibia 7. The articular insert 40 is attached to the fixation member 24 and is between the tibia 7 and the femur 8. When the patient walks, the femoral component 50 is pressed into the bearing surface 44 with great force which can reach several times the patient's body weight. In a second type of prosthetic implant, as seen in FIG. 11, the fixation member is in the form of a acetabular cup. The acetabular cup 60 attaches to a patient's pelvis 62. The acetabular cup 60 has a convex surface 64 which fits against the patient's pelvis 62. The concave surface 66 of the acetabular cup 60 is constructed to receive an articular insert 40'. A hip stem 68 attaches to the patient's femur 70. The hip stem 68 has a ball 72 which fits into the articular insert 40'. Again, when the patient is walking, the articular insert 40' is subject to great compressive force due to the ball 72 pressing into the articular insert 40'.

In either embodiment, the fastener 10 tends to be forced in an opposite direction relative to the fixation member 24 due to its rigid attachment to the bone. The uppermost thread 22 pushes against the underside 28 of the fixation member 24 and will not move relative to the fixation member 24. Thus, the inside surface 42 of the articular insert 40 does not come into contact with the head member 12 because the uppermost thread 22 will not move past the underside 28 of the fixation member 24. Therefore, damage to the articular insert 40 is prevented.

What is claimed is:

1. A non-backing fixation device for a prosthetic implant comprising:
    a fastener of a unitary construction having a head member and a shank, said head member having an underside and an upperside;
    and said shank having threads along its length, said threads having an outside diameter greater than the width of said head member and said shank having an uppermost thread adjacent to said head member; and
    a fixation member having an upperside and underside and a bore therethrough for receiving said fastener, said bore having a diameter intermediate the width of said head member and said outside diameter of said threads of said shank such that, when said fastener is inserted into said bore, to a position wherein said head member is received into said bore and a compressive force is applied to said fixation member, and when said fixation member moves relative to said fastener, said uppermost thread contacts said underside of said fixation member, to prevent said fastener from backing out.

2. The fixation device of claim 1 wherein said underside of said head member is spherical and said upperside is flat.

3. The fixation device of claim 2 wherein said upperside has a chamfered edge.

4. The fixation device of claim 3 wherein said fixation member is a base plate for use in a prosthetic knee.

5. The fixation device of claim 1 wherein said upperside and underside of said head member are flat and perpendicular to an axis of symmetry of said fastener.

6. The fixation device of claim 1 wherein said upperside of said head member is spherical and said underside of said head is flat and perpendicular to an axis of symmetry of said fastener.

7. The fixation device of claim 1 wherein said fixation member is a base plate for use in a prosthetic knee.

8. The fixation device of claim 1 wherein said fixation member is an acetabular cup for use in a prosthetic hip.

9. The fixation device of claim 1 wherein said bore includes a spiral recess defining internal threads for cooperation with said threads of said shank said recess terminating immediately above said underside of said fixation member such that a lip is formed where said recess meets said underside of said fixation member for contacting said uppermost thread of said fastener to prevent said fastener from backing out of said fixation member.

* * * * *